(12) United States Patent
Shao et al.

(10) Patent No.: US 9,376,357 B2
(45) Date of Patent: Jun. 28, 2016

(54) METHOD FOR PREPARING HIGH-CONTENT ZEAXANTHIN

(71) Applicant: Zhejiang Medicine Co., Ltd., Xinchang Pharmaceutical Factory, Shaoxing, Zhejiang (CN)

(72) Inventors: Bin Shao, Zhejiang (CN); Lihua Zhang, Zhejiang (CN); Xinde Xu, Zhejiang (CN); Xiaoxia Sun, Zhejiang (CN)

(73) Assignees: ZHEJIANG MEDICINE CO., LTD., Xinchang, Shaoxing; XIECHANG PHARMACEUTICAL FACTORY, Shaoxing, Zhejiang (CN)

( * ) Notice: Subject to any disclaimer, the term of this patent is extended or adjusted under 35 U.S.C. 154(b) by 0 days.

(21) Appl. No.: 14/412,170

(22) PCT Filed: Jul. 9, 2013

(86) PCT No.: PCT/CN2013/079069
§ 371 (c)(1),
(2) Date: Dec. 30, 2014

(87) PCT Pub. No.: WO2014/008851
PCT Pub. Date: Jan. 16, 2014

(65) Prior Publication Data
US 2015/0175510 A1    Jun. 25, 2015

(30) Foreign Application Priority Data

Jul. 12, 2012 (CN) .......................... 2012 1 0241214

(51) Int. Cl.
C07C 29/56 (2006.01)
C07C 403/24 (2006.01)
B01J 31/02 (2006.01)

(52) U.S. Cl.
CPC ................ *C07C 29/56* (2013.01); *B01J 31/02* (2013.01); *C07C 403/24* (2013.01); *C07B 2200/13* (2013.01); *C07C 2101/16* (2013.01)

(58) Field of Classification Search
CPC ...................................................... C07C 29/56
See application file for complete search history.

(56) References Cited

U.S. PATENT DOCUMENTS

| 5,780,693 | A  | * | 7/1998  | Bernhard et al. | 568/816 |
| 6,376,722 | B1 | * | 4/2002  | Sanz et al.     | 568/816 |
| 6,420,614 | B1 | * | 7/2002  | Eugster et al.  | 568/816 |
| 6,818,798 | B1 | * | 11/2004 | Khachik         | 568/816 |
| 7,485,738 | B2 | * | 2/2009  | Xu et al.       | 554/125 |

OTHER PUBLICATIONS

Database CAPLUS in STN, Acc. No. 2012:511983, Lu et al., CN 102399178 A (Apr. 4, 2012) (abstract).*
Database CAPLUS in STN, Acc. No. 2008:613945, Wu et al., CN 101182302 A (May 21, 2008) (abstract).*
Database CAPLUS in STN, Acc. No. 2007:211677, Tao et al., CN 1915970 A (Feb. 21, 2007) (abstract).*

* cited by examiner

*Primary Examiner* — Brian J Davis
(74) *Attorney, Agent, or Firm* — Tianhua Gu; Global IP Services

(57) ABSTRACT

The invention discloses a method for preparing high-content zeaxanthin. In the conventional preparation methods, some methods adopt certain toxic organic solvents; some methods require the multi-step crystallization process; and some methods are featured by long reaction time, high temperature and lower product yield, thus being not suitable for industrial production. The invention adopts lutein crystal or its fatty acid ester as the raw material and utilizes isomerization reaction to produce zeaxanthin, and is characterized in that a mixed catalyst consisting of an organic base catalyst and a cocatalyst is used in the isomerization reaction, wherein the cocatalyst is palladium carbon. The invention has the advantages of simple process route, low reaction temperature, short reaction time, good product purity and high yield, thus being suitable for industrial production, and no poisonous and harmful organic solvent residues in the product, thus being suitable for the use as a food additive or drug.

16 Claims, No Drawings

METHOD FOR PREPARING HIGH-CONTENT ZEAXANTHIN

CROSS REFERENCE TO RELATED PATENT APPLICATION

The present application is the US national stage of PCT/CN2013/079069 filed on Jul. 9, 2013, which claims the priorities of the Chinese patent applications No. 201210241214.9 filed on Jul. 12, 2012, which applications are incorporated herein by reference.

FIELD OF THE INVENTION

The invention relates to a method for preparing high-content zeaxanthin through catalytic isomerization reaction of lutein crystals extracted from natural plants or its fatty acid ester.

BACKGROUND OF THE INVENTION

Zeaxanthin is a variety of oxygenated carotenoid widely present in nature, and is an important colorant and a component with unique physiological functions. Zeaxanthin and lutein are isomers and are the only two varieties of carotenoids present in the human retina, which have the main difference in different positions of the double bonds at their terminals, and their structural formulae are as follows.

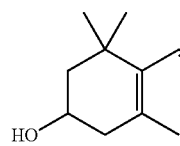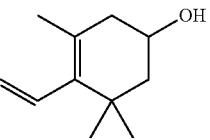

Zeaxanthin (Molecular Formula: C40H56O2 Molecular Weight: 568.85)

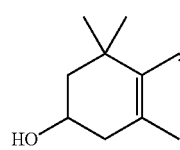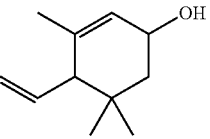

Lutein (Molecular Formula: C40H56O2 Molecular Weight: 568.85)

Zeaxanthin has an important function for eye health, its mechanism of action comprises two aspects, the first is filtration of high-energy blue light in visible light, zeaxanthin can absorb near-ultraviolet blue light, the blue light has great damage to the photoreceptors and retinal cells in eyes; the second is anti-oxygenation, 11 conjugated double bonds are contained in the molecular structure of zeaxanthin, have strong oxidation resistance, can quench singlet oxygen and scavenge free radicals, and inhibit oxidative damage to the retina, crystalline lens and other tissues caused by various reasons; in addition, because the number of conjugated double bonds in the molecular structure of zeaxanthin is more than that of lutein, zeaxanthin has stronger antioxidant capacity than that of lutein, and may play a more important role in human eye health.

Zeaxanthin and lutein together constitute the only two varieties of carotenoids existing in human eyes and play an important role in human eye health. However, zeaxanthin cannot be synthesized in human body and must be taken from the outside, and the amount of zeaxanthin in human body will gradually decrease with age growth, therefore it is very necessary to supplement high-quality zeaxanthin products suitable for edible use of human through diet or dietary supplements.

In the prior art, the sources of zeaxanthin can basically be divided into three categories: full chemical synthesis method, fermentation method, and lutein isomerization method. The disadvantages of the full chemical synthesis method lie in that usually a lot of reaction steps are required, the reaction conditions are harsh with many side reactions, and the yield of the final product is low; microbes used in the fermentation method are mainly flavobacterium cells, the disadvantages of the fermentation method for production of zeaxanthin lie in that most microbes have lower fermentation unit, and the fermented product is required to be subjected to more complicated subsequent extraction and purification steps; and compared with the above two methods, zeaxanthin produced through the lutein isomerization method is regarded as a promising method, because this process involves only one reaction, and the product yield is higher and the purity is good under the premise that reaction conditions are controlled. However, many difficulties exist in the conversion process from lutein to zeaxanthin, and only one or two manufacturers can realize industrial production of zeaxanthin by using this method so far, this is because the isomerization reaction is required to be carried out in a strongly alkaline environment at higher temperature, and the stronger alkalinity is, the higher the temperature is, the better the reaction will be; but the reaction substrate lutein and the reaction product in this reaction are very unstable carotenoids, they are very unstable under a strongly alkaline and high-temperature environment, and are easy to be degraded or even carbonized. Thus, in order to pursue a high conversion rate during the reaction, a large amount of strong base would have to be used to react at a higher temperature, which will cause part of lutein and part of resulting zeaxanthin to be degraded and carbonized, therefore reaction yield is very low. In most patents previously disclosed, the production yield of zeaxanthin by way of lutein isomerization is generally about 30%, thus being far less than the requirement of industrial production.

PCT Patent Publication WO96/02594 relates to a method for producing zeaxanthin in the strongly basic solution through isomerization of lutein under the conditions of controlled temperature and pressure. But its highest yield is 24%, thereby being not suitable for industrial production.

U.S. Pat. No. 5,780,639 (Authorized Chinese Patent Publication No. CN 1082507 C) discloses a process route of producing zeaxanthin by adopting lutein as the raw material, in which the mixture of dimethyl sulphoxide or saturated alkane and/or aromatic hydrocarbon organic solvent is mainly taken as the solvent, and alkali metal hydroxide is taken as the catalyst for transposition of lutein, so as to produce zeaxanthin. This process has the disadvantages that the amount of base used is large, the reaction time is long, the product yield is low (product yield obtained by the method is less than 30% shown in repeated tests), thereby being not suitable for industrial production. Moreover, n-hexane, n-heptane, dichloromethane, methanol and other organic solvents are used during the reaction, production of food-grade or pharmaceutical-grade zeaxanthin by using these toxic solvents are clearly inappropriate.

Authorized Chinese Patent Publication No. CN 101182302 B discloses a method for preparing a composition containing zeaxanthin, which mainly adopts the scheme that isomerization of lutein is performed to prepare zeaxanthin under the catalytic action of the base catalyst and cocatalyst consisting of (formic acid, acetic acid, oxalic acid, propionic acid or sodium borohydride). This process has the disadvantages that the reaction time is long and 12-36 hr is required, the content of the final product is 30-80%, and recrystallization treatment is required to be carried out if the product with higher content is needed. Furthermore, because hexane, heptane, methanol, benzene, toluene and other organic solvents are used in the reaction process, these solvents are not suitable for use in food.

U.S. Pat. No. 7,485,738 B2 (Authorized Chinese Patent Publication No. CN 101153017 B) relates to method for preparing food-grade zeaxanthin through epimerization under the catalysis of strong organic base by using lutein as the raw material. This process has the disadvantages that the reaction time is relatively long (8-15 hr), and the yield is 60%.

To sum up, the methods described in the above patents have several disadvantages: 1) some toxic organic solvents are used in the process, these solvents are difficult or impossible to be completely removed, resulting in unsuitability for human to eat the product; 2) the multi-step crystallization process is required in order to obtain high-content crystals; and 3) the reaction time is long, the temperature is high, some reaction materials and reaction products are degraded during the reaction, and the product yield is relatively low, thus being not suitable for industrial production.

Therefore, it is necessary to find a method suitable for scale industrial production of high-content zeaxanthin, less toxic organic solvents and procedures should be used in this process as much as possible, the amount of strong base should be minimized as much as possible, to shorten the reaction time and reduce the reaction temperature, but a higher reaction yield can be obtained, and the resulting product is suitable for human consumption.

SUMMARY OF THE INVENTION

The invention aims to solve the technical problem by overcoming the defects existing in the prior art, and provides a method suitable for preparing high-content edible zeaxanthin featured by mild reaction conditions, high product yield, and no product recrystallization and other purification treatment through industrial production.

To this end, the invention adopts the following technical scheme to achieve: a method for preparing high-content zeaxanthin, in which zeaxanthin is obtained through isomerization reaction by taking lutein crystals or its fatty acid esters as the raw material. The method is characterized in that a mixed catalyst consisting of an organic base catalyst and a cocatalyst is used in the isomerization reaction, and the cocatalyst is palladium carbon. The experimental results show that the use of the cocatalyst in the above reaction can help reduce the activation energy of reaction, shorten the reaction time, reduce the reaction temperature, and improve the conversion of lutein and the reaction yield.

The mechanism of action palladium-carbon cocatalyst is as follows: Pd is complexed with double-bond electron cloud on 4',5' carbon atoms on the benzene ring at the terminal of a lutein molecule, the energy required for proton capture by terminal carbon is greatly reduced, the requirement for a strongly basic environment is lowered, and the proton is easier to migrate from a negative carbon ion site (6' carbon atom) to another site (4' carbon atom), thus accelerating the double bond to transfer from 4',5' carbon positions to 5',6' positions, achieving the purpose of converting lutein into zeaxanthin, reducing the amount of base used, and greatly shortening the reaction time.

The specific steps for the method of preparing high-content zeaxanthin are as follows:

① Add lutein crystals or its fatty acid esters as the reaction raw material in an organic solvent, to be sufficiently dissolved at a temperature of 60-95° C.;

② Add an organic base catalyst and a cocatalyst into the mixed liquid obtained in Step ① to carry out isomerization reaction, wherein the organic base catalyst is added dropwise;

Perform incubated reaction under nitrogen protection (i.e. in an inert environment);

④ Dilute the reaction solution obtained in Step ③ with the mixed solution of deionized water and ethanol, and separate to obtain crystals by using the conventional separation methods;

⑤ Dissolve the crystals obtained in Step ④ in ethyl acetate, and filter;

Add the mixed solution of deionized water and ethanol into the filtrate obtained in Step, and filter after stirring;

⑦ Vacuum-dry crystalline obtained in Step ⑥, to obtain zeaxanthin crystals.

The purpose of Step is to recover the palladium-carbon cocatalyst. In the mixed solution of deionized water and ethanol, the volume percentage occupied by ethanol is 30-90%; and the conventional separation methods are suction filtration, pressure filtration, centrifugation, etc.

In order to protect the lutein as the reaction material and the resulting zeaxanthin from being oxidized, an inert environment is required to be created during the reaction, that is, nitrogen is filled into the reaction system for protection. In the process of separation of crystals, continuously rinse with water and ethanol until the effluent liquid is nearly colorless, and perform vacuum-drying to obtain zeaxanthin crystals; and analyze the content of total carotenoids in the product by adopting UV-visible spectrophotometry and the proportion of zeaxanthin and lutein in the total carotenoids by way of high-performance liquid chromatography.

In the above method for preparing high-content zeaxanthin, sodium methoxide, sodium ethoxide, potassium methoxide or ethanol potassium is preferably selected as the organic base catalyst.

In the above method for preparing high-content zeaxanthin, the amount of the organic base catalyst added is 4-8 times the molar mass of the reaction material; the amount of the cocatalyst added is 0.1-5.0% the mass of the reaction material; and ethylene glycol, propylene glycol, or the mixed solvent of ethylene glycol and propylene glycol is selected as the organic solvent.

In the above method for preparing high-content zeaxanthin, the isomerization reaction temperature is between 60-95° C., and is preferably between 60-75; and the isomerization reaction time is preferably between 2.0-8.0 h.

In the above method for preparing high-content zeaxanthin, lutein fatty acid ester or lutein crystals as the reaction raw material used is derived from marigold flowers, wherein the former is obtained by refining marigold oleoresin, and the latter is crystals obtained after saponification treatment of marigold oleoresin.

The content of total carotenoids in the product obtained through the above method is more than 80%, the product yield is high and is up to 70% above, zeaxanthin accounts for about 90% of the content of total carotenoids, purification treatment like re-crystallization is not required, therefore the method has the advantages of simplified process, suitability for industrial production, and no poisonous and harmful organic solvent residues detected in the product, thus being suitable for the use as a food additive or drug.

DETAIL DESCRIPTION OF THE INVENTION

The invention is further illustrated by the following embodiments, which are used only for describing the technical scheme of the invention rather than limiting the invention.

Embodiment 1

Weigh 30 g of lutein crystals (the content of total carotenoids accounts for 88.5%, in which the proportions of lutein and zeaxanthin in the total carotenoids are respectively 91.5% and 7.3%, and the rest is a small amount of other carotenoids) to be mixed with 360 ml of ethylene glycol, stir to dissolve at 60, add 0.03 g of palladium carbon, drop 42.4 ml of 5.0 mol/L sodium methoxide solution, complete dropwise addition of base catalyst in 45 min, sample and analyze the proportions of lutein and zeaxanthin in the reaction solution every 0.5 hr after performing nitrogen protection and incubated reaction at 60 for 2.0 h, to obtain the proportion of 90.5% zeaxanthin in the total carotenoids in the reaction solution through measurement after 4.5 hr. Lower the temperature of the reaction solution to 70, add with the mixed solution of 1000 ml of deionized water and 600 ml of food-grade ethanol and stir to dilute the reaction solution, separate the diluted reaction solution through suction filtration, filter after dissolving the filter cake with 1000 ml of ethyl acetate, recover palladium carbon, add the mixed solution of 500 ml of deionized water and 300 ml food-grade ethanol, perform suction filtration after stirring for 0.5 hr, rinse the filter cake with the mixed solution of water and ethanol in the filtration process until the eluate is near colorless, and perform vacuum-drying of the filtrate to obtain 22.1 g of orange crystalline. The content of total carotenoids in the crystalline is 85.7% through analysis by way of UV-visible spectrophotometry, the yield of total carotenoids is 71.3%, wherein zeaxanthin accounts for 91.1% in the total carotenoids, and lutein accounts for 6.0% in the total carotenoids.

The product does not contain toxic organic solvents, thereby being suitable for being used in the form of nutritional supplements and food additives. Application of the crystalline may be in the forms of oil suspension (mixed and emulsified with vegetable oil), beads (microcapsules obtained through spraying and condensation), dry powder (microcapsules obtained through spraying and drying), etc.

Comparative Embodiment 1

Weigh 30.3 g of lutein crystals (the content of total carotenoids accounts for 88.5%, in which the proportions of lutein and zeaxanthin in the total carotenoids are respectively 91.5% and 7.3%, and the rest is a small amount of other carotenoids) to be mixed with 360 ml of ethylene glycol, stir to dissolve at 75, drop 42.4 ml of 5.0 mol/L sodium methoxide solution, complete dropwise addition of base catalyst in 45 min, lower the temperature of the reaction solution to 70 after performing nitrogen protection and incubated reaction at 60 for 4.5 hr, add with the mixed solution of 1000 ml of deionized water and 600 ml of food-grade ethanol and stir to dilute the reaction solution, separate the diluted reaction solution through suction filtration to crystallize, rinse the filter cake with the mixed solution of water and ethanol in the filtration process until the eluate is near colorless, and perform vacuum-drying of the filtrate to obtain 24.7 g of orange crystalline. The content of total carotenoids in the crystalline is 79.6% through analysis by way of UV-visible spectrophotometry, the yield of total carotenoids is 74.1%, wherein zeaxanthin only accounts for 67.4% in the total carotenoids, lutein accounts for 28.5% in the total carotenoids, and some lutein is still not completely converted to zeaxanthin.

The difference between the comparative embodiment 1 and the embodiment 1 lies in that cocatalyst is not added in the comparative embodiment, and other experimental conditions are the same. As can be seen from the experimental results, under the same reaction conditions, the cocatalyst is conductive to improving the conversion rate of lutein, and making the proportion of zeaxanthin in the final product meet the requirements within shorter reaction time.

Embodiment 2

Weigh 50.6 g of lutein fatty acid ester obtained by refining marigold oleoresin (wherein the content of fatty acid ester in total carotenoids accounts for 78.2%, the proportions of lutein and zeaxanthin in the total carotenoids are respectively 93.4% and 6.1%, and the rest is a small amount of other carotenoids) to be mixed with 400 ml of propylene glycol, stir to dissolve at 95, add 2.53 g of palladium carbon, drop 71.1 ml of 5.4 mol/L sodium ethoxide solution, and sample and analyze the proportions of lutein and zeaxanthin in the reaction solution every 0.5 hr after performing nitrogen protection and incubated reaction at 95 for 4 hr, to obtain the proportion of 91.3% zeaxanthin in the total carotenoids in the reaction solution through measurement after 8.0 hr. Stop reacting, lower the temperature of the reaction solution to 70, add with the mixed solution of 1000 ml of deionized water and 600 ml of food-grade ethanol and stir to dilute the reaction solution, centrifugally separate the diluted reaction solution, filter after dissolving the filter cake with 1500 ml of ethyl acetate, recover palladium carbon, add the mixed solution of 500 ml of deionized water and 300 ml food-grade ethanol, perform suction filtration after stirring for 0.5 hr, rinse the filter cake with the mixed solution of water and ethanol in the filtration process until the eluate is near colorless, and perform vacuum-drying of the filtrate to obtain 19.5 g of orange crystalline. The content of total carotenoids in the crystalline is 83.4% through analysis by way of UV-visible spectrophotometry, the yield of total carotenoids is 76.1%, wherein zeaxanthin accounts for 92.1% in the total carotenoids, and lutein accounts for 6.3% in the total carotenoids, both of them are in free form.

Comparative Embodiment 2

Weigh 50.8 g of lutein fatty acid ester obtained by refining marigold oleoresin (wherein the content of fatty acid ester in total carotenoids accounts for 78.2%, the proportions of lutein and zeaxanthin in the total carotenoids are respectively 93.4% and 6.1%, and the rest is a small amount of other carotenoids) to be mixed with 400 ml of propylene glycol, stir to dissolve at 95, drop 82.0 ml of 5.4 mol/L sodium ethoxide solution, sample and analyze the proportions of lutein and zeaxanthin in the reaction solution every 0.5 hr after performing nitrogen protection and incubated reaction at 95 for 4 hr, to obtain the proportion of 76.7% zeaxanthin in the total carotenoids in the reaction solution through measurement after 8.0 hr and the proportion of 89.8% zeaxanthin in the total carotenoids after continuing to react for 4.5 hr, stop reacting, lower the temperature of the reaction solution to 70, add with the mixed solution of 1000 ml of deionized water and 600 ml of food-grade ethanol and stir to dilute the reaction solution, centrifugally separate the diluted reaction solution, filter after dissolving the filter cake with 1500 ml of ethyl acetate, recover palladium carbon, add the mixed solution of 500 ml of deionized water and 300 ml food-grade ethanol, perform suction filtration after stirring for 0.5 hr, rinse the filter cake with the mixed solution of water and ethanol in the filtration process until the eluate is near colorless, and perform vacuum-drying of the filtrate to obtain 14.4 g of orange crystalline. The content of total carotenoids in the crystalline is 80.2% through analysis by way of UV-visible spectrophotometry, the yield of total carotenoids is 53.8%, wherein zeaxanthin accounts for 91.3% in the total carotenoids, and lutein accounts for 6.0% in the total carotenoids, both of them are in free form.

The difference between the comparative embodiment 1 and the embodiment 1 lies in that cocatalyst is not added in the comparative embodiment, in order to react fully, under the condition that the amount of base is increased, the reaction time is extended to 12.5 hr with the reaction temperature at 95, part of carotenoids is degraded in incubation process at this temperature for a long time, which can be seen from the yield of the final product. As can be seen from the experimental results, the cocatalyst is conductive to reducing the isomerization reaction temperature, shortening the reaction time, and improving the conversion rate of lutein.

Embodiment 3

Weigh 45 g of lutein crystals (the content of total carotenoids accounts for 88.5%, in which the proportions of lutein and zeaxanthin in the total carotenoids are respectively 91.5% and 7.3%, and the rest is a small amount of other carotenoids) to be mixed with 350 ml of ethylene glycol and propylene glycol, stir to dissolve at 60, add 1.13 g of palladium carbon, drop 80.0 ml of 6.0 mol/L methanolic potassium solution, and complete dropwise addition of base catalyst in 50 min, to obtain the proportion of 88.7% zeaxanthin in the total carotenoids in the reaction solution through measurement after performing nitrogen protection and incubated reaction at 75 for 2.0 hr. Lower the temperature of the reaction solution to 70, add with the mixed solution of 1000 ml of deionized water and 600 ml of food-grade ethanol and stir to dilute the reaction solution, separate the diluted reaction solution through suction filtration, filter after dissolving the filter cake with 1200 ml of ethyl acetate, recover palladium carbon, add the mixed solution of 500 ml of deionized water and 400 ml food-grade ethanol, perform suction filtration after stirring for 0.5 hr, rinse the filter cake with the mixed solution of water and ethanol in the filtration process until the eluate is near colorless, and perform vacuum-drying of the filtrate to obtain 34.9 g of orange crystalline. The content of total carotenoids in the crystalline is 86.2% through analysis by way of UV-visible spectrophotometry, the yield of total carotenoids is 75.7%, wherein zeaxanthin accounts for 90.1% in the total carotenoids, and lutein accounts for 8.4% in the total carotenoids.

What is claimed is:

1. A method for preparing zeaxanthin comprising adopting lutein crystals or its fatty acid esters as raw materials and utilizing an isomerization reaction to obtain zeaxanthin, wherein a mixed catalyst consisting of an organic base catalyst and a cocatalyst is used in the isomerization reaction, and the cocatalyst is palladium carbon.

2. The method for preparing zeaxanthin of claim 1, wherein the steps of the method are as follows:
   a) adding lutein crystals or its fatty acid esters as the raw materials in an organic solvent, to be dissolved at a temperature of 60-95° C.;
   b) adding the organic base catalyst and the cocatalyst into the mixed solution obtained in step a) to carry out an isomerization reaction, wherein the organic base catalyst is added dropwise;
   c) performing a reaction under nitrogen protection;
   d) diluting the reaction solution obtained in Step c) with a mixed solution of deionized water and ethanol, and separating thereafter to obtain crystals by using separation methods;
   e) dissolving the crystals obtained in Step d) in ethyl acetate, and filtering thereafter;
   f) adding a mixed solution of deionized water and ethanol to the filtrate obtained in Step e), and filtering after stirring;
   g) performing vacuum-drying of the crystals obtained in Step f), to obtain zeaxanthin crystals.

3. The method for preparing zeaxanthin of claim 1, wherein the organic base catalyst is sodium methoxide, sodium ethoxide, potassium methoxide or potassium ethoxide.

4. The method for preparing zeaxanthin of claim 1, wherein the amount of organic base catalyst added is 4-8 times the molar mass of the raw materials.

5. The method for preparing zeaxanthin of claim 1, wherein an amount of cocatalyst added is 0.1-5.0% of the mass of the raw materials.

6. The method for preparing zeaxanthin of claim 2, wherein ethylene glycol, propylene glycol, or a mixed solvent of ethylene glycol and propylene glycol is chosen as the organic solvent.

7. The method for preparing zeaxanthin of claim 1, wherein the isomerization reaction temperature is between 60-95° C.

8. The method for preparing zeaxanthin of claim 7, wherein the isomerization reaction temperature is between 60-75° C.

9. The method for preparing zeaxanthin of claim 1, wherein the isomerization reaction time is between 2.0-8.0 h.

10. The method for preparing zeaxanthin of claim 1, wherein lutein fatty acid ester or lutein crystals as the raw materials is derived from marigold flowers, wherein the former is obtained by refining marigold oleoresin, and the latter is crystals obtained after saponification treatment of marigold oleoresin.

11. The method for preparing zeaxanthin of claim 2, wherein the organic base catalyst is sodium methoxide, sodium ethoxide, potassium methoxide or potassium ethoxide.

12. The method for preparing zeaxanthin of claim 2, wherein the amount of organic base catalyst added is 4-8 times the molar mass of the raw materials.

13. The method for preparing zeaxanthin of claim 2, wherein the amount of cocatalyst added is 0.1-5.0% of the mass of the raw materials.

14. The method for preparing zeaxanthin of claim 2, wherein the isomerization reaction temperature is between 60-95° C.

15. The method for preparing zeaxanthin of claim 2, wherein the isomerization reaction temperature is between 60-75° C.

16. The method for preparing zeaxanthin of claim 2, wherein the isomerization reaction time is between 2.0-8.0 h.

* * * * *